United States Patent [19]

Quinn et al.

[11] Patent Number: 5,227,485
[45] Date of Patent: Jul. 13, 1993

[54] PYRAZOLO[3,4-D]PYRIMIDINES WITH ADENOSINE-LIKE BINDING AFFINITIES

[75] Inventors: Ronald J. Quinn; Michael J. Dooley; Peter J. Scammells; Mary Chebib, all of Brisbane, Australia

[73] Assignee: Griffith University, Queensland, Australia

[21] Appl. No.: 717,202

[22] Filed: Jun. 19, 1991

[30] Foreign Application Priority Data

Jun. 19, 1990 [AU] Australia ............................... PK0691

[51] Int. Cl.$^5$ ........................................... C07D 487/04
[52] U.S. Cl. .................................... 544/262; 536/27.6
[58] Field of Search ......................................... 544/262

[56] References Cited

FOREIGN PATENT DOCUMENTS 688770  6/1984  Canada .
366284  2/1963  Switzerland .
366840  3/1963  Switzerland .

OTHER PUBLICATIONS

Tominaga et al., *J. Heterocyclic Chem.*, 27, 775–783 (1990).
Quinn et al., *Aust. J. Chem.*, 44, 753–757 (1991).
Brown et al., *Aust. J. Chem.*, 32, 453–458 (1979).
Davies et al. (I), *Eur. J. Pharmacology*, 97, 325–329 (1984).
Davies et al. (II), *Life Sci.*, 34(22), 2117–2128 (1984).
Davies et al. (III), *Neurosci Lett.*, 41(1–2), 189–193 (1983).

*Primary Examiner*—Johnnie R. Brown
*Assistant Examiner*—L. Eric Crane
*Attorney, Agent, or Firm*—Nixon & Vanderhye

[57] ABSTRACT

The A21 receptor extracelluar site and the A2 receptor extracellular site of adenosine analogues are structurally different and that binding orientations of adenosine or adenosine analogues are different at these sites and this may be used to determine their structure. Novel pyrimidine compounds are described.

3 Claims, 8 Drawing Sheets ively different at these sites. The specification hereinafter

PYRAZOLO[3,4-D]PYRIMIDINES WITH ADENOSINE-LIKE BINDING AFFINITIES

This invention relates to a method of determination of the structure of chemical compounds and compounds determined or formed by this method.

In particular, the invention relates to adenosine analogues or adenosine related compounds such as adenosine mimics whereby such analogues may have their structure determined by the method of the present invention.

Adenosine is a naturally occurring endogenous nucleoside which has generated much interest due to its biological activity. Much of this activity is mediated via extracellular receptors which bind adenosine and its analogues which may include compounds such as alkylxanthines and other miscellaneous heterocycles. This is reported in Williams M TINS 164–168 (1984) Daly J W J. Med Chem 25(3) 197–207 (1982) and Davies L P et al Life Sciences 34 2117–2128 (1984).

The present invention has now discovered that the A1 receptor extracellular site and the A2 receptor extracellular site are structurally different and that binding orientations of adenosine or adenosine analogues are different at these sites. The specification hereinafter illustrates this discovery using Quantitative Structural Activity Relationships (QSAR) and computer graphic analyses on a broad spectrum of ligands. These techniques are discussed in CHEM-X, developed and distributed by Chemical Design Ltd Oxford, England.

The N6 substituted compounds PIA, CPA and N6-norbornyl adenosine were fitted by aligning N9, N6 and atoms of ribose. The cyclopentyl and phenylisopropyl side chains have little energy barrier to rotation about the C6-N6 bond, however the global minimum energy conformation of N6-norbornyl adenosine presents the five-membered ring of the norbornane ring just 1.19A from the plane of the heterocycle and above the imidazole ring, with substantial energy barriers to rotation.

Figure 2:
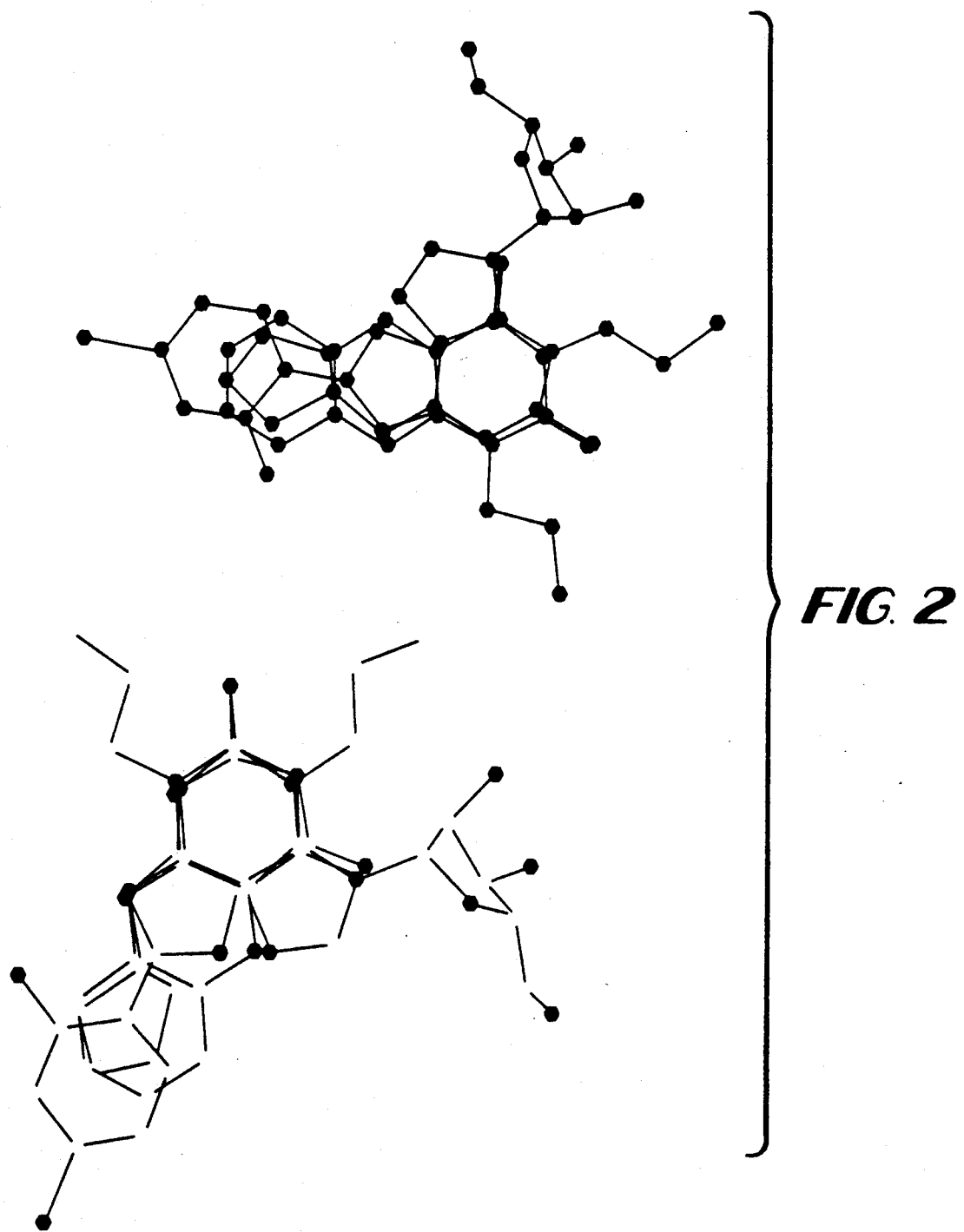

FIG. 2: CPA, alloxazine and PACPX

In the case of alloxazine, the fused phenyl ring is necessarily in the plane of the heterocycle and this may also be the case with PACPX due to partial double bond character of the C8-phenyl bond. These compounds were fitted to CPA by aligning the hydrophobic groups and maximizing the correlations between the atoms of the heterocycle.

Figure 3:
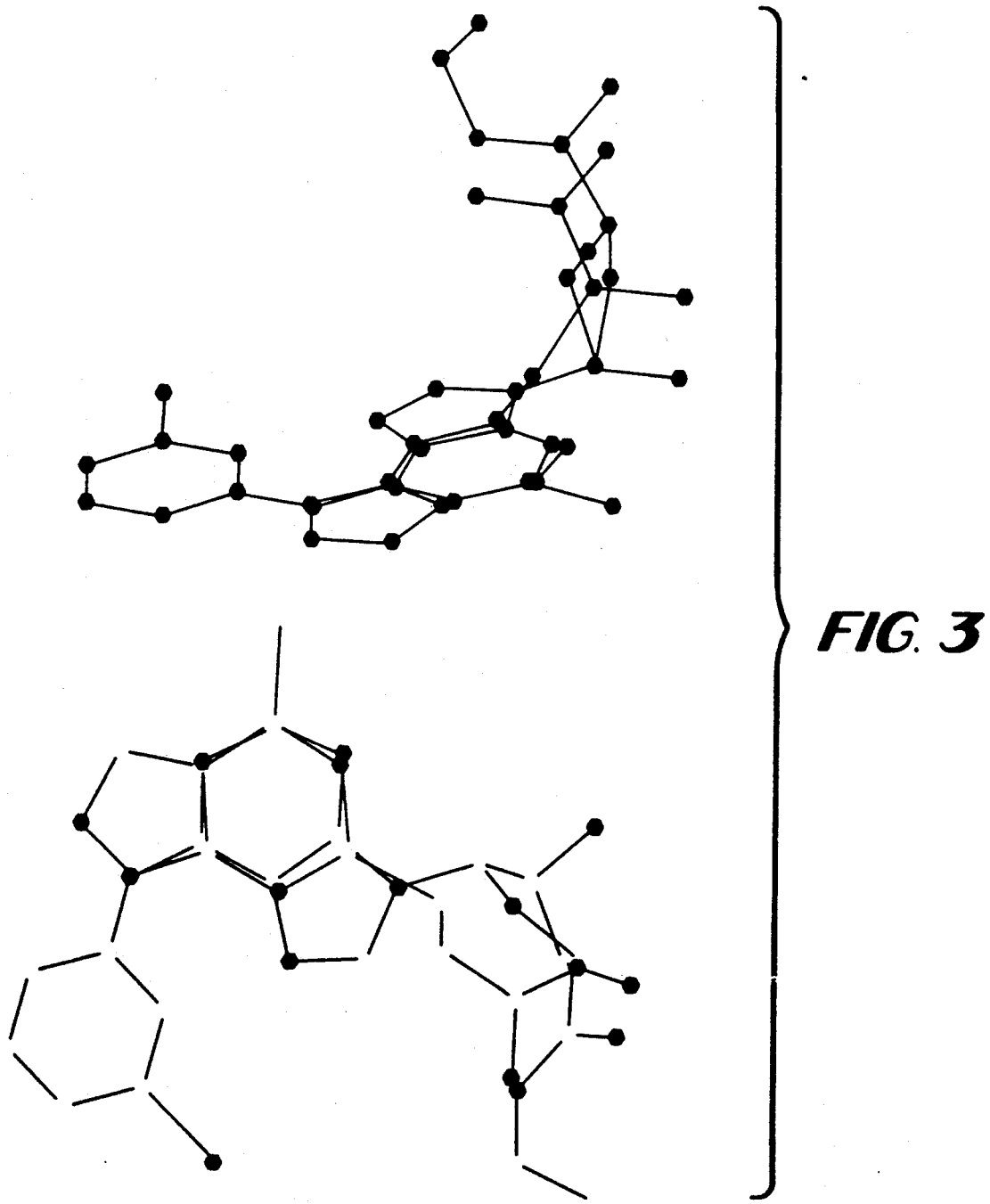

FIG. 3: NECA and pyrazolo[3,4-d]pyrimidine

This figure illustrates how the pyrazolo[3,4-d]pyrimidine orientates relative to NECA. Interestingly, the amide functionalities of both may be in close proximity while in energetically feasible conformations.

Figure 4:
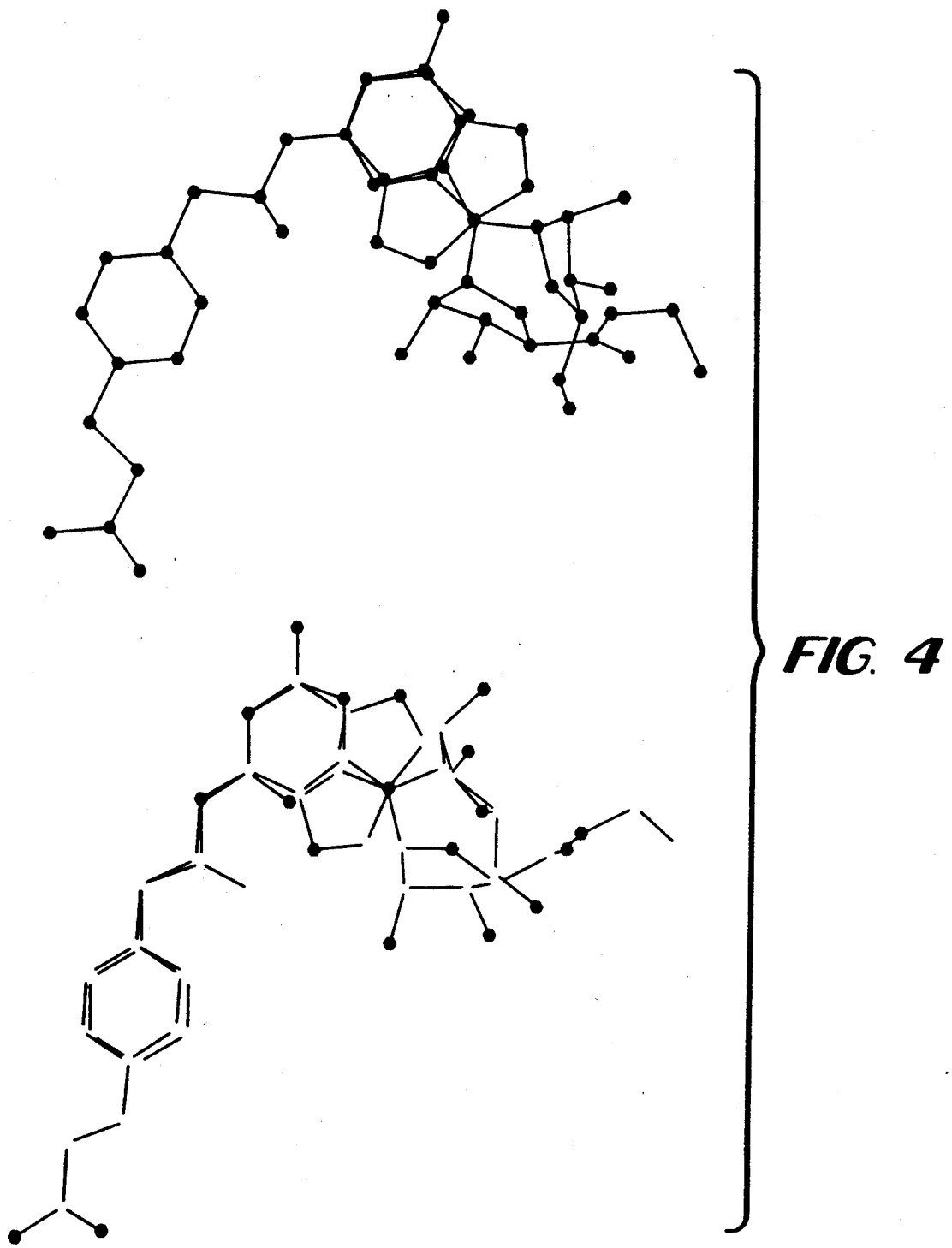

FIG. 4: CGS21680 and PIA

The altered orientation of a C-2 substituted compound (CGS21680) relative to an N6 substituted compound (PIA) is illustrated. These compounds were fitted by aligning hydrophobic groups and maximizing correlations between atoms of the heterocycle. The ribose moieties, although in different orientations occupy the same area. This may play a role in selectivity. The ribose binding domain of the A2 receptor may have twisted with respect to the A1 site and thus favorably bind ribose in the altered orientation.

Figure 5:
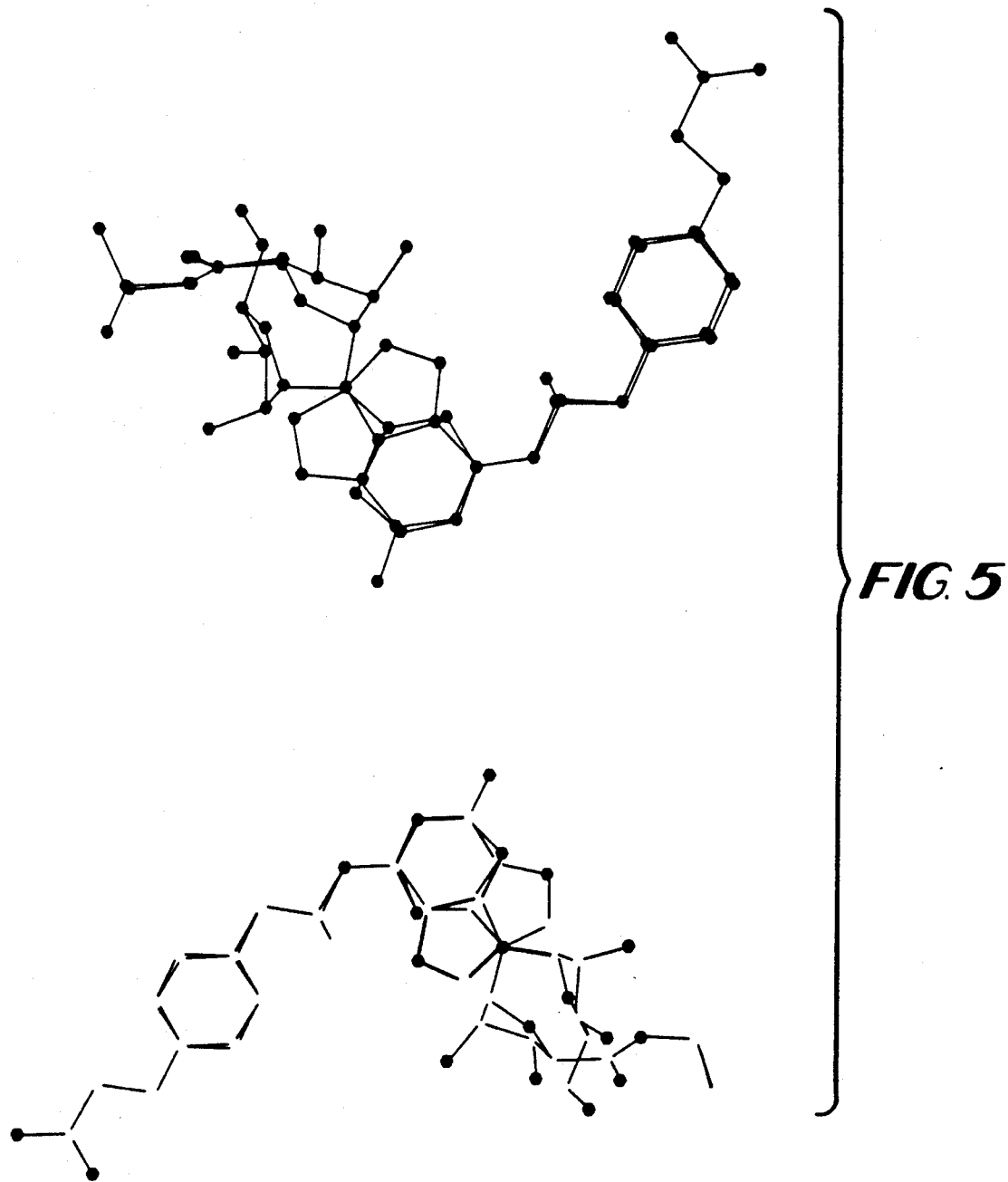

FIG. 5: NECA, PIA and CGS21680

This diagram illustrates how NECA, PLA and CGS21680 align at the A2 site. Note that the ribose of PIA is unable to occupy the same position as CGS21680 and this possibly explains the reduced agonistic activity of PIA at the A2 site. Note also that NECA is able to adopt a different orientation at the A2 site than at the A1 site and is therefore capable of non-selective agonism.

Figure 6B:
Figure 6A:
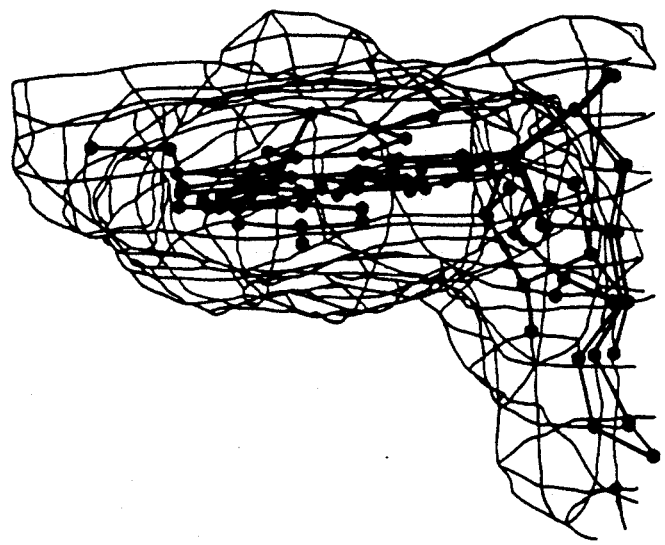

FIG. 6A relates to the superimposition of all 8 adenosine analogues referred to in FIGS. 1–5 (i.e., PIA, CPA, N6-norbornyl adenosine, alloxazine, PACPX, NECA, pyrazolo [3,4-d]pyrimidine and CGS 21680) in the receptor excluded volume of the A1 and A2 receptors (i.e. the spaces available within the receptor sites which can be occupied by the adenosine analogues) from one particular orientation.

FIG. 6B relates to the superimposition of all 8 adenosine analogues referred to in FIGS. 1–5 (i.e. PIA, CPA, N6-norbornyl adenosine, alloxazine, PACPX, NECA, pyrazolo [3,4-d]pyrimidine and CGS 21680) in the receptor excluded volume of the A1 and A2 receptors (i.e. the spaced available within the receptor sites which can be occupied by the adenosine analogues) in an orientation different to that shown in FIG. 6A.

Figure 6D:
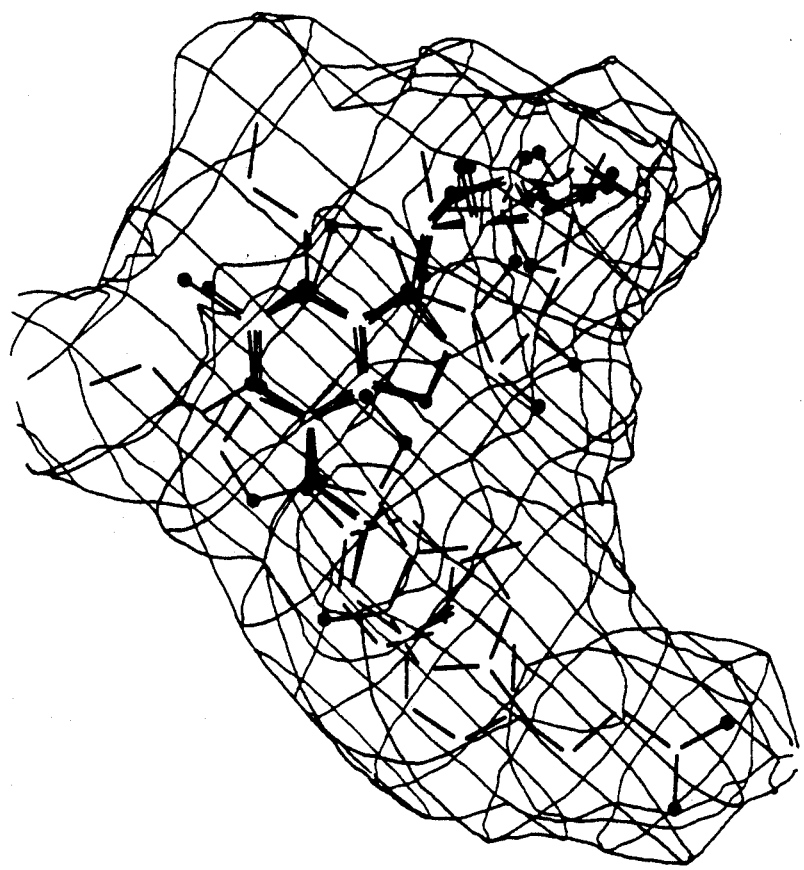
Figure 6C:
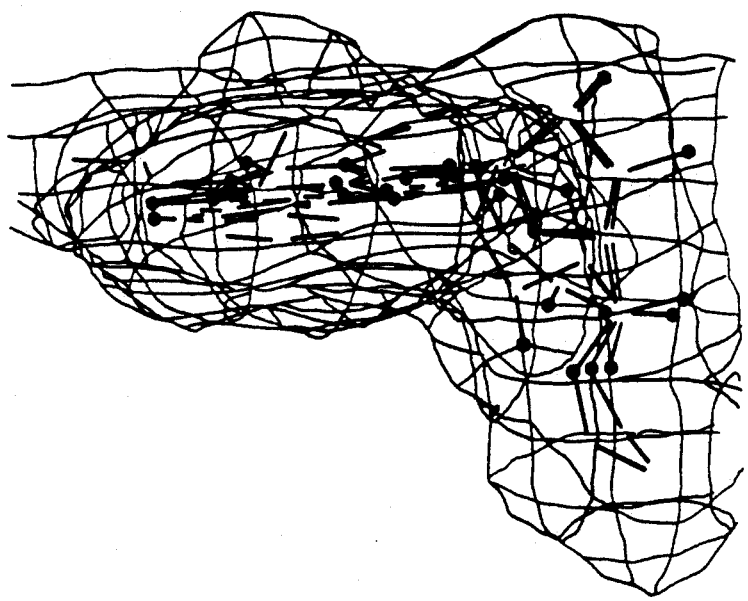

FIG. 6C refers to the superimposition of all 8 compounds as described in FIG. 6A but with the carbon atoms omitted; and FIG. 6D relates to the superimposition of all 8 adenosine analogues as described in FIG. 6B but with the carbon atoms omitted.

Figure 7:
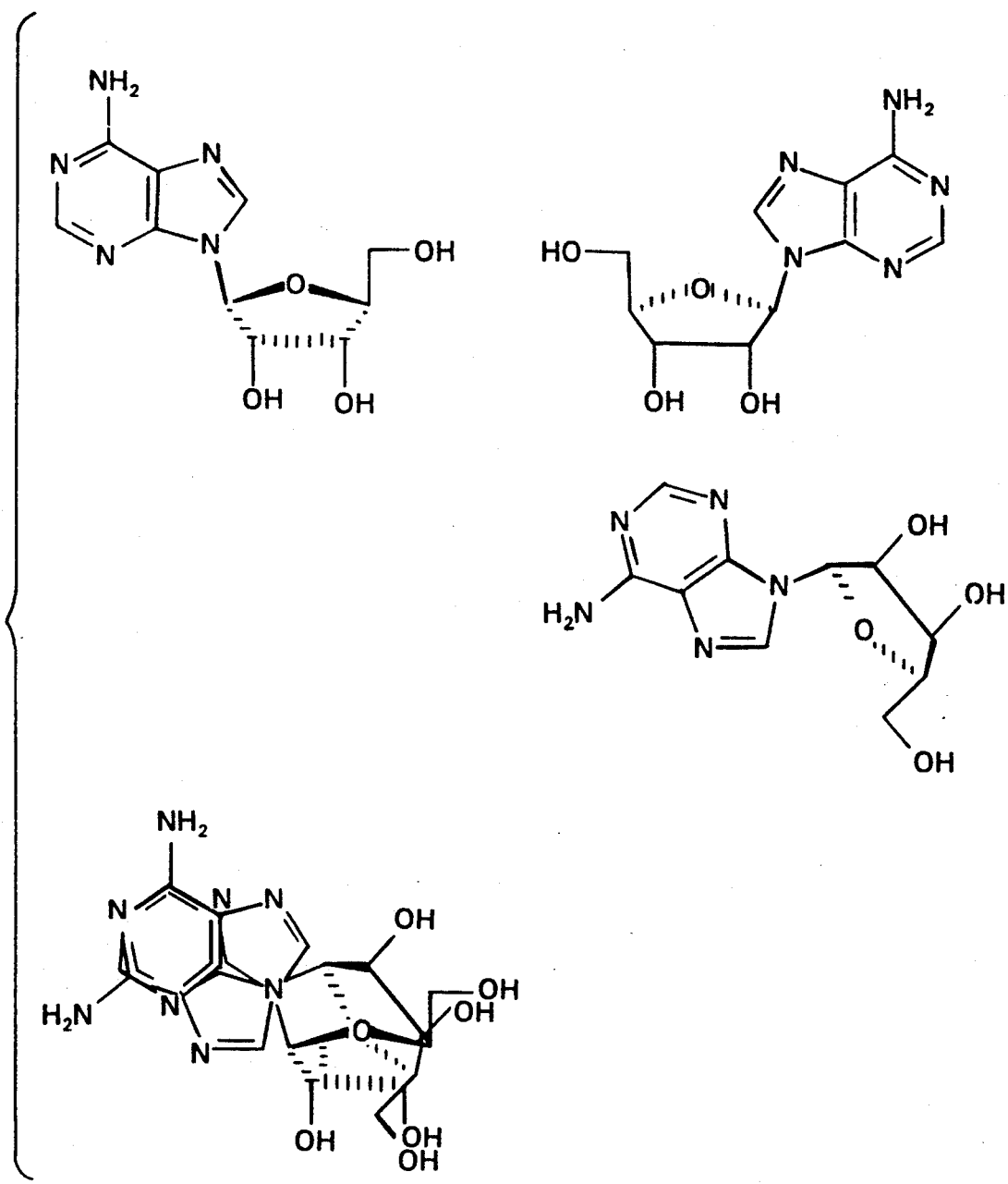

FIG. 7 shows the relative orientation of adenosine at the A1 and A2 receptors, (a) placing the purine ring of adenosine in the X,Y plane as shown in 3a shows the orientation of the A2 receptor; the relative orientation at the A1 receptor is obtained by (b) a Y axis rotation of 180° to give 3b (c) a Z axis rotation of about 130° to give 3c (d) superimposition of 3a and 3c, as shown in 3d, shows the relative orientation of adenosine at the A1 and A2 receptors.

DETAILED DESCRIPTION OF THE INVENTION

To explain in more detail the nature of the A1 and A2 receptor sites, it is necessary to realise that the A1 receptor sites occur on one type of cell and the A2 receptor site occurs on another type of cell. In other words, A1 and A2 receptors, as far as is known at the present time, do not occur on the same cell. A2 receptor sites occur in heart cells, all brain cells, endocrine gland cells, blood elements and vasculature while A1 receptor sites also occur in brain cells, heart cells and fat cells. A2 receptor sites can be classified into low affinity binding sites and high affinity binding sites.

Adenosine, which was discovered 60 years ago, has profound hypotensive, antispasmodic, sedative and vasodilatory activity [Drury A. N et al J. Physiol. 68 213–32 (1929)]. Many of these functions are mediated by the A1 and A2 receptors thereby altering the level of intracellular 3′,5′-cyclic AMP. The nature of these receptors is reported in detail in Williams above. However, so far to date only very limited work has been carried out on the nature of these receptor sites. One report (Hamilton H. W et al J. Med. Chem 30 91–96 1987) determined that the binding orientation of a series of pyrazolo[4,3-d]pyrimidines relative to various 8-aryl alkylxanthines at the A1 receptor site is directed by the substituents present and the nitrogens of the respective heterocycles. This reference also found that these respective compounds bind at the A1 receptor site in a reversed orientation relative to one another.

The role of adenosine in modifying the physiological function and cyclic AMP concentration in a large variety of cell types by interacting with external receptors is described in Burnstock G. Circ. Res. 46 175-182 (1980) and Londos C. et al Proc. Natl. Acad. Sci USA 77 2251-4 (1980). Effects on nervous tissue function include (1) modulation of adenylate cyclase activity (Daly J. Med Chem 25 197-207 1982);
(2) inhibition of both nerve cell firing and neurotransmitter release in vivo and in vitro [Harms H. H. et al Neuropharmacol 18 577-580 (1979) and Barraco R. A. et al Brain Res. 272 392-395 (1983)]; and
(3) a sedative action in the whole animal thought to be centrally mediated Katims J. J. et al J. Pharmacol. Exp. Theraps 227 167-173.

For adenylate cyclase systems 5'-N-ethyl carboxamidoadenosine (NECA) is a more potent agonist at A2 surface receptors than is R-$N^6$-phenylisopropyl adenosine (R-PIA) whereas the reverse potency order is seen with A1 surface receptors. The A1 receptor has a high affinity binding site for adenosine ($\sim 10^{-9}$M) while the A2 receptor has a low affinity binding site for adenosine ($\sim 10^{-6}$M). These effects are blocked by the alkylxanthines. A third type of adenosine biding site, the P site, is located intracellularly on the catalytic subunit of the cyclase and inhibits cAMP formation. This site is not antagonised by the alkylxanthines (Daly above).

1-methylisoquanosine was previously isolated during a programme investigating the biologically active constituents of marine organisms [Quinn R. J. et al Tetrahedron Letters 21 567-8, Davies et al Life Sciences 26 1079-1088 (1980); Norton et al J. Chem. Soc. Chem. Comm. 339-341 (1980); Cook et al J. Org. Chem. 45 4020-4025 (1980); and Gregson J. Carbohyd. Nucleotides and Nucleosides 8 345-362 (1981)]. A crude extract of the sponge *Tedania digitata* displayed muscle relaxant, antihypertensive and antiflammatory properties and the constituent responsible for all of the pharmacological actions was proven to be 1-methylisoguanosine. When given to mice either by the oral or intraperitoneal it caused potent muscle relaxation and hypothermine.

In other in vivo tests it reduced blood pressure and heart rate in rates [Baird-Lambert J. A. et al Life Sciences 26, 1069-1077-1980] and blocked polysynaptic responses in the mouse spinal cord at doses in which transmission at the neuromuscular junction was unaltered [Buckle et al Naunyn. Schmiedeb. Arch. Pharmacol. 316 64-68 (1981) and York et al. Can. J. Physiol. Pharmacol 60 302-307 (1982)]. It is not completely clear whether the muscle-relaxation is a direct central effect due to purinergic depression of cell firing or whether it may be secondary to a signifcnat fall in blood pressure; Phillis and Wu Physiology and Pharmacology of Adenosine Derivatives p219-236 Raven Press New York (1983) have suggested that blood pressure falls in animals can cause secondary effects on the firing of central neurons.

Biochemical data show that 1-methylisoguanosine is resistant to degradation by adenosine deaminase, is a poor substrate for, or inhibitor of, the adenosine uptake system (nucleoside transporter), and can interact with extracellular adenosine receptors, i.e. the A1 and A2 sites. It appears that this metabolically stable adenosine analogue can remain in the extracellular environment of cells for sufficient time to activate adenosine receptors and cause various pharmacological effects. It may be noted that while adenosine itself has minimal or no effects when given to animals by the intraperitonial route, in the presence of an adenosine uptake inhibitor and/or an adenosine deaminase inhibitor, it can cause muscle relaxation and hypothermia [Davies et al Gen Pharmacol. 13 27-33 (1982)].

Interestingly, 1-methylisoguanosine can interact with benzodiazepine receptors (Ki of approximately 17 $\mu$M vs $^3$H-diazepam binding, Kd=11 nM), being several hundred fold more potent than inosine and hypoxanthine, two purines which have been suggested as possible benzodiazepine receptor ligands in the brain [Davies, Baird Lambert et al The Physiology and Pharmacology of Adenosine Derivatives Raven Press New York p 257-266 (1983)].

Like diazepam, 1-methylisoquanosine decreases cerebellar levels of cyclic GMP (Davies, Baird Lambert et al above) confirming observations that alterations in behavioural (or peripheral muscle) activity can influence cerebellar cyclic GMP content.

Adenosine has been implicated in the mechanisms involved in anxiety, analgesia, sleep, and preliminary evidence indicates that it has a role in depression [Williams Handbook of Neurochemistry Second Edition p1-26 Plenum Press New York (1983)]. In a recent study R-PIA had effects on mouse locomotor activity at 1/10th the doses required to elicit cardiovascular effects (Katims et al above). The evidence supporting a neuromodulatory role for adenosine in the CNS is considerably more extensive than that for many of the peptides found in brain tissue [Williams Trends Neuro Sci 164-168 (1984)]. Adenosine may interact with the central systems involved in analgesia and anxiety as part of a non-specific homeostatic mechanism indicating that a therapeutic role for an adenosine agonist would be as a sedative or somnificant, while an antagonist would conversely be a central stimulant (Williams Trends Neuro Sci above). The effects of adenosine on acetylcholine turnover have been shown to have regional specificity and broncho-selective alkylxanthines such as enprofylline indicate the possibility of tissue differences in adenosine related recognition systems (Williams Trends Neuro Sci above).

Adenosine may be the brain's natural anticonvulsant. It is involved in the spontaneous arrest of epileptic seizures and is brought into play by the seizure itself [Dragunow Trends in Pharm Sci 128-129 (1986)]. NECA displayed slightly more anticonvulsant activity than R-PIA in reductions of amygdaloid-kindled seizures in rats [Barraco et al Neurosci. Lett. 18 317-22 (1984)]. The rank order of potency of adenosine agonists in increasing the seizure threshold of pentylenetetrazol induced seizures was consistent with involvement of adenosine receptors [Murray et al Neuropharmacology 24 761-6 (1985)]. Adenosine has also been shown to be a putative mediator in asthma and adenosine-induced bronchoconstriction is selective for allergic and asthmatic subjects [Church et al Trends in Pharm. Sci 49-50 (1986].

Adenosine causes relaxation of coronary vascular smooth muscle [Olsson et al Cir. Res. 45 468-478 (1979)], coronary arteries appear to contain A2 receptors (Londos et al above) and noradrenaline-contracted guinea pig aorta is relaxed by adenosine by interactions with A2 receptors [Collis et al Eur. J. Pharmacol. 96 61-69 (1983)]. The negative inotropic and chronotropic responses of adenosine analogues in the isolated guinea pig atria is typical of A1 receptors while the coronary vasodilatory effect investigated in the isolated heart is typical of A2 receptors (Leunget al Aust. Soc. Clin. Exp. Pharmacologists 18th Ann. Meeting, Melbourne Dec. 5–7, 1984).

A series of N6-substituted adenosines have been used to model the N6 receptor sub-region [Kusachi et al J. Med. Chem. 28 1636–1643 (1985)]. A review of the two classes of cell surface adenosine receptors has appeared [Daly Adv. Cyclic Nucleotide Protein Phosphorylation Res. 19 29–43 (1984)]. The division of the A2 receptor site into two sub classes, as discussed above, was suggested in Kusachi et al above.

An object of the present invention is to provide a method of determination of the structure of a novel adenosine analogue based upon the binding characteristics of adenosine or an adenosine analogue which may be different to the novel adenosine analogue and which may include a known structure at both an A1 receptor site and an A2 receptor site.

A further object of the invention is to determine from the nature of such structure whether the adenosine analogue will be an agonist or an antagonist at the receptor site.

In this regard, according to Biochemistry by David E Metzler, Academic Press New York (1977), an agonist may be regarded as a metabolite or drug which may bind to an appropriate cell surface receptor and which triggers a response in the cell whereas an antagonist is a metabolite or drug of related structure which may bind to the cell surface receptor but fails to elicit a response. Agonists and antagonists often act in a strictly competitive fashion as in competitive inhibition of enzyme action.

With the above objects in mind, the method of the invention includes the following steps:

(i) determination of how adenosine or a particular adenosine analogue will bind at an A2 site by characterising the relevant binding sites of the adenosine or adenosine analogue, or alternatively the binding sites of the A2 receptor;

(ii) determination of how the adenosine or adenosine analogue will bind at an A1 site by characterising the relevant binding sites of adenosine or the adenosine analogue, or alternatively the binding sites of the A1 receptor;

(iii) comparing the orientation of adenosine or the adenosine analogue at the A2 site with the orientation of adenosine or the adenosine analogue at the A1 site by a process of superimposing each orientation with respect to each other so as to determine which part of the molecule is conserved and which part is nonconserved; and (iv) determining the structure of the adenosine analogue from the results of step (iii) and optionally (v) determining whether the adenosine analogue will be agonist or antagonist from such structure.

Arising from the above steps, the present invention has discovered structural differences between the A1 receptor site and the A2 receptor site.

Although, not wishing to be bound by any particular theory, it would seem that when adenosine is bound at the A1 site its orientation relative to adenosine bound at the A2 site is defined by means that adenosine rotates through an angle of 180° about the 4,5 bond subsequently followed by a rotation in the plane of the heterocyclic ring of about 130°. This is illustrated in FIG. 7 hereinafter.

It would also seem, in accordance with the present invention, that adenosine analogues will bind at three binding sites: a single hydrophobic binding site, a central aromatic binding site and a ribose binding site. The relationship between the three binding domains is fixed in space. The binding domains have a certain relationship to each other which is illustrated in the compounds whose structure is provided hereinafter.

In regard to the A2 site, it is believed that the hydrophobic binding site is such that adenosine or adenosine analogue may occupy an orientation depicted below, i.e.

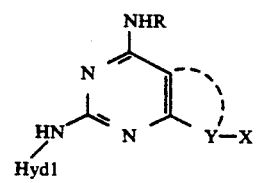

where Hyd1 is the hydrophobic group and R is a relatively small substituent. Y is derived from the 5 membered ring of adenosine and X is a group being ribose, derived from ribose or a ribose replacement group.

In the A1 site the orientation of adenosine or the adenosine analogue is believed to be

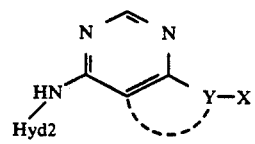

where Hyd2 is a hydrophobic group smaller than Hyd1 and Y and X have the meanings given before.

In the A1 and also the A2 positions, Y can be open or closed.

In the A1 position when X is ribose or derived from ribose the orientation of the ribose moiety is

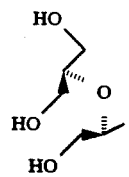

In the A2 position, where X is ribose or derived from ribose, the orientation of the ribose moiety is

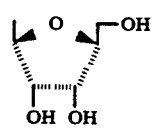

In the foregoing, when adenosine or the adenosine analogue are superimposed upon each other the six membered rings are substantially conserved and the six membered rings can bear any appropriate substituents. It will also be appreciated that the nitrogens in the heterocycle can be replaced by other suitable atoms, e.g. S or C.

Figure 1:
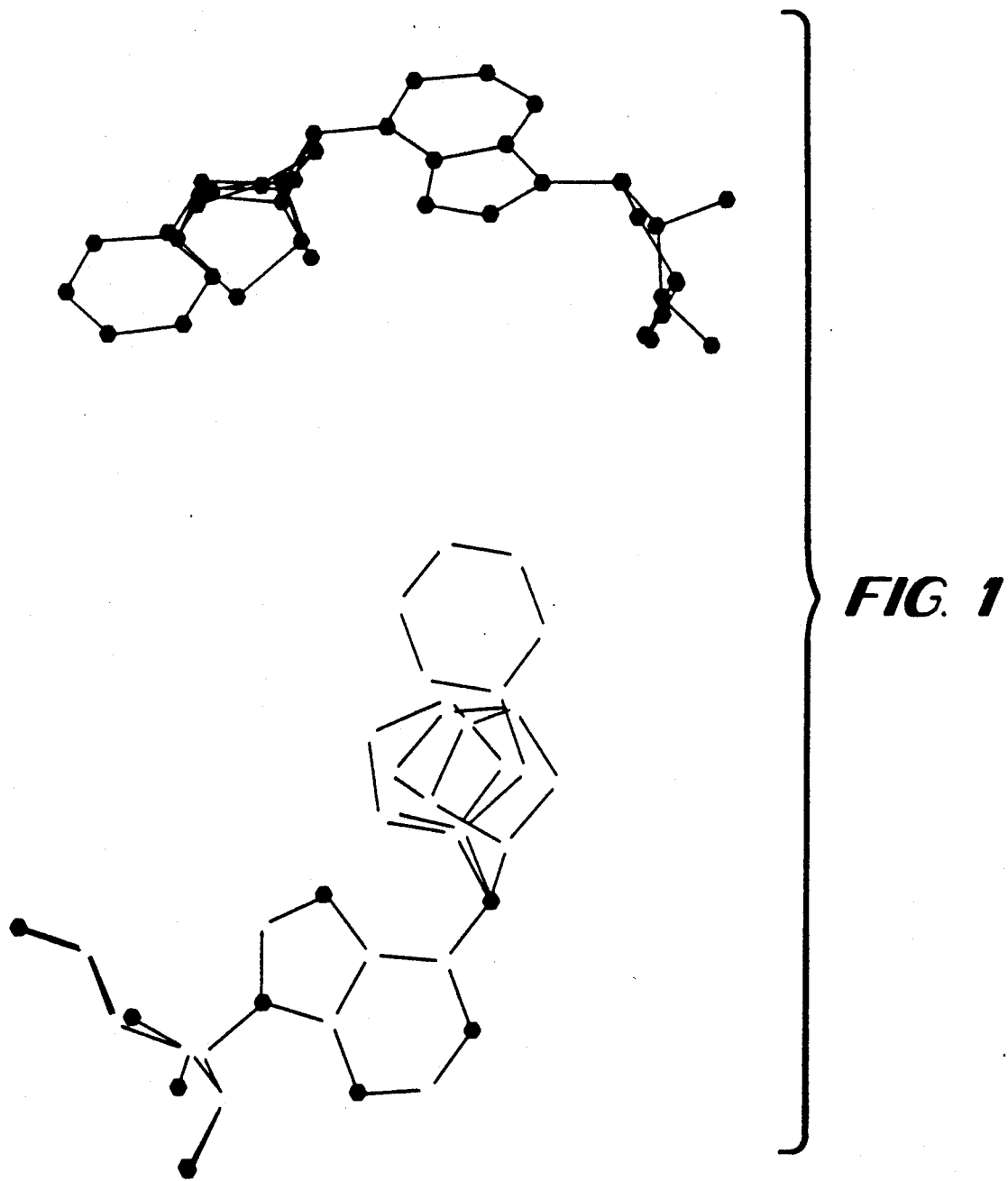
FIG. 1: PIA, CPA and N6-norbornyl

Most compounds in accordance with this invention were constructed or determined by computer graphic analyses as discussed previously and by making the necessary modifications to the X-ray crystal data of closely related compounds (e.g. alkylxanthines from caffeine and adenosine analogs from adenosine) using standard bond angles and lengths. In some cases (e.g. substituted pyrazolo [3,4-d] pyrimidines) the compound was constructed using standard bond angles and lengths. Initially, the binding orientation of N6 substituted compounds at the A1 and A2 site was determined by inspection of the QSAR's of a number of N6 substituted adenosine analogs where N9 (in relation to comparing activity of adenosine and 9-deazadenosine) ribose was found to be involved in binding to the receptor. This was reported in Bruns et al Mol. Pharm. 29 331–346 (1986). It was also found that the C2 and C5 hydroxyls were also involved in binding activity (Taylor et al J. Med. Chem. 32, 346–353 (1986). Also, the N6 proton Trivedi et al J. Med. Chem. 1667–1673 (1989) and one hydrophobic substituent Trivedi et al J. Med. Chem. 32 8–11 (1989) were also found to be involved in binding at the receptor. In the procedure of the invention N6 substituted adenosine analogs were allowed to relax to their global minima by employing an MM2 optimisation. They were fitted to minimize the RMS distance between the pairs of atoms responsible for binding (a minimum of three points is required; we chose N6,N9 and ribose) as shown in FIG. 1. The sidechain of the compound N6-(1R, 2S, 4S) endo-norbornyl-adenosine (see Trivedi et al above J Med Chem 32 11–13 1989) was found to be in a minimum energy conformation as illustrated, with substantial energy barriers to rotation about C6-N6. This defines the position of the N6 hydrophobic binding domain.

A number of antagonists (alkylxanthines, substituted pyrazolo [3,4-d] pyrimidines, alloxazine) were introduced into this system. These were fitted considering the hydrophobic groups as directing binding and then obtaining maximum correlation between heterocycles. The result is illustrated in FIG. 2. This confirms the position of the N6 hydrophobic group since the aromatic rings of these compounds are necessarily in the same plane as the heterocycle. A fit of 1-phenyl-6-propionamidylthio-4-thiopyrazolo [3,4-d] pyrimidine and NECA oriented to align the purine ring of NECA with the purine ring of CPA as in FIGS. 1 and 2 shows (FIG. 3) that the amide functionalities of both are capable of occupying approximately the same region in space. The orientation of the hydrophobic group of the pyrazolo [3,4d-] pyrimidine is identical to that shown for the hydrophobic groups in FIGS. 1 and 2 and is the only one which allows the close proximity of the amide groups.

From the lack of additivity between N6 and C2 hydrophobic substituents [Trivedi et al J. Med. Chem. 32(8) 1667–1673 (1989)], it can be deduced in accordance with this invention (among other explanations) that there is only one hydrophobic binding site at the A1 and A2 sites. This supports directing binding of hydrophobic groups into a single binding domain as a method of fitting molecules. This gives rise to a completely different binding orientation for compounds with a C-2 hydrophobic substituent such as 2-aminophenyl adenosine and CGS21680 relative to the N6 substituted compounds. In this case, the points used to fit the molecules were: N9, N2, and the hydrophobic substituent (FIG. 4). The altered position of the ribose in C2 substituted compounds suggests that the ribose binding domain of the A2 site may have moved slightly with respect to the heterocycle binding domain and its position in the A1 site. We would expect therefore that A2 selective N6-substituted compounds (e.g. N6-2-diphenylethyl compounds) although able to bind strongly to the A2 site may have reduced agonistic activity. It is apparent that the heterocyclic rings are not fully conserved, indeed while the superimpositions define the six-membered ring of the heterocycle as being conserved the five membered ring is not needed in entirety. This also starts to illustrate that only certain of the ring nitrogens may be necessary for binding.

The compounds adenosine and NECA are non-selective and are good agonists at both sites suggesting that they are capable of binding in different orientations at the A1 and A2 sites. FIG. 5 illustrates the orientation of PIA, CGS21680 with NECA oriented to align the purine ring of NECA with the purine ring of CGS21680 as at the A2 site. At the A1 site, the purine ring of NECA would be aligned with PIA. The receptor excluded volume of the A1 and A2 receptors are very similar. The alignment of adenosine within the receptor binding site would be controlled by specific interaction between adenosine and the protein side chains. FIG. 6 shows the orientation of adenosine analogues within the receptor excluded volume at the A1 and A2 sites.

From the foregoing, a number of novel compounds may be determined. Consistent with the six-membered ring of the heterocycle being conserved, we have found that (1) possesses moderate affinity for the A1 receptor. The orientation of the alkylxanthines places O6 close to the N9 position of the adenosines. The compound (2) should therefore bind in the same orientation as the alkylxanthines as directed by the ribose, thus it should be an agonist. Similarly, (3) with a ribose in the C-5 position of 3-phenyltriazolo [4,5-d] pyrimidine will place it in the correct position to bind into the ribose binding domain and convert the triazolo [4,5-d] pyrimidine from an antagonist into an agonist.

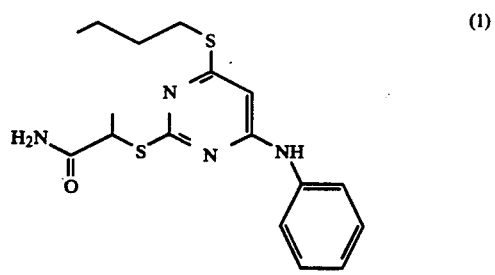

(1)

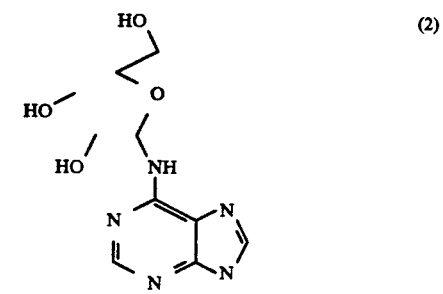

(2)

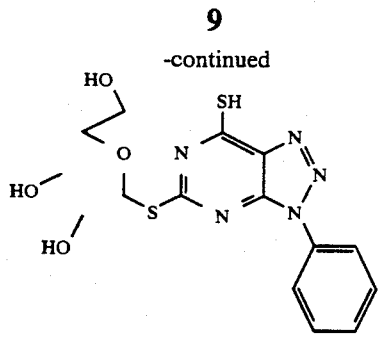
(3)

The multipoint system we have developed allows the rationalisation of structure-activity relationships of many adenosine receptor ligands. It illustrates how the binding orientation of N6 substituted compounds is fundamentally different to the C2 substituted compounds at both receptors, defining characteristics that may be involved in selectivity. The potential for adenosine and NECA to bind in different orientations at the two sites is also illustrated.

The present invention also includes those novel molecules derived from the above system, an example of which is compound 1, (2-n-butylthio)-4-(N-phenyl)-6-propionamidyl thiopyrimidine which possesses moderate affinity for the A1 receptor. Compound 1 was prepared as follows:

A suspension of 0.3 g (1.15 mmol) 3-phenyl-1,2,3-triazolo [4,5-d]-5,7-dithio-pyrimidine in 15 ml of dry THF was sealed under nitrogen and stirred in a dry ice - methanol bath (−70° C). To this suspension was added 1.8 ml (2.8 mmol) n-butyl lithium (1.6M in hexane). To this solution was added a solution of 0.35 g (2.3 mmol) 2-bromopropionamide and 15 ml of dry THF over a period of 20 in. After 45 min, TLC analysis (hexane-ethyl acetate 1/1) indicated the reaction was complete. The reaction mixture was quenched with water (10 ml), allowed to warm to room temperature and partition between chloroform and water. The organic layer was washed consecutively with 1M NaOH (3×10 ml), 1M HCl (3×10 ml), and water (3×10 ml), dried over anhydrous magnesium sulphate for 60 min, filtered and reduced under vacuum to leave a brown oil (0.25 g). The oil was flash-chromatographed (ethyl acetate-hexane 1-1) on a 3×10 cm column and the fractions containing the single product with approximately 0.6 (in the above solvent system) were pooled and reduced under vacuum to give a pink crystalline compound (crude yield 0.065 g). The material was recrystallized from ethyl acetate to give 0.050 g of compound 1. Compound 1 has the following properties:

m.p.: 142.7°–143.1° C.

$^1$H NMR (CDCl$_3$): δ 0.91 (3H,t,CH$_3$,J 7.5 Hz); δ 1.42 (2H,sextet,CH$_2$); δ 1.56 (3H,d,CH$_3$,J 7.5 Hz); δ 1.61 (2H, quintet, CH$_2$); δ 3.06 (2H,ABX$_2$ system J-AB 13.1 Hz, J-AX 7.2 Hz, J-BX 7.2 Hz, δA 3.1, δB 3.01); δ 4.37 (1H,q,C-H,J 7.5 Hz); δ 5.75 (1H,s(broad),amide N-H); δ 6.31 (1H,s,C-H); δ 7.06 (1H,s(broad),amide N-H); δ 7.17–7.41 (5H,m,Aromatic H); δ 7.52 (1H,s(broad),N-H).

$^{13}$C NMR (CDCl$_3$): δ13.49 (CH$_3$); δ 16.34 (CH$_3$); δ 21.81 (CH$_2$); δ 29.29 (CH$_2$); δ 31.29 (CH$_2$); δ 41.55 (C-H); δ 95.66 (C-H); δ123.01 (C2',C6'); δ 125.51 (C4'); δ 129.63 (C40',C5'); δ 137.67 (C1'); δ 159.62 (Q); δ 169.32 (Q); δ 170.00 (Q); δ 175.27 (C=O).

I.R. Spectrum: 3340 cm$^{-1}$ (N-H broad); 3180, 3230 cm$^{-1}$ (N-H); γ 2970, 2960, 2940 cm$^{-1}$ (aliphatic C-H stretch); γ 1680 cm$^{-1}$ (carbonyl); γ 1620, 1550, 1540 cm$^{-1}$ (aromatic C stretch). U.V. Spectrum (MeOH): λmax 252,305 nm (e=26780, 16380); base shift: λmax 252,306 nm; acid shift: λmax 248,311 nm.

COMPOUND 4

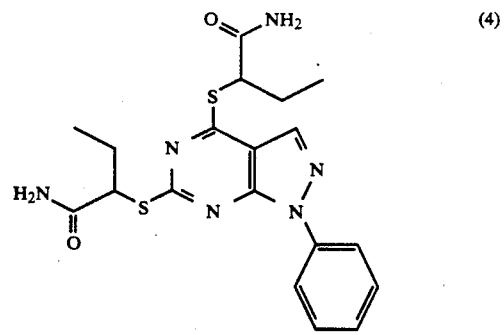
(4)

Hydrophobic Binding Domain—Phenyl ring.
Central Aromatic Binding Domain—Pyrimidine ring.
Ribose Binding Domain—Amide side chain (C6).
The IC$_{50}$ at the A$_1$ receptor ($^3$H-PIA) is 1.08 (±0.01)×10$^{-7}$M.

4,6-bis-α-carbamoylpropylthio-1-phenylpyrazolo[3,4-d]pyrimidine

1-Phenyl-5H,7H-pyrazolo[3,4-d]pyrimidin-4,6-dithione[1] (0.50 g, 1.9 mmol) was dissolved in sodium hydroxide (1M, 10 ml). 2-bromobutanamide (3.8 mmol) was added and the reaction was stirred at room temperature for 24 hours. A solid precipitated and was collected by suction filtration. Recrystallisation of the crude product from DMSO and water afforded pure 4,6-bis-α-carbamoylpropylthio-1-phenylpyrazolo[3,4-d]pyrimidine: yield 71%: mp 195°–198° C.

[1]E. C. Taylor, A. Mckillop and R. N. Warrener, *Tetrahedron*, 1967, 23, 891.

$^1$H NMR (d$^6$DMSO) δ 0.98 (t, 3, J 7.2 Hz, CH$_3$); δ 1.01 (t, 3, J 7.2 Hz, CH$_3$); δ 1.94 (m, 4, 2×CH$_2$); δ 4.34 (q, 1, J 6.8 Hz, CH); δ 4.70 (q, 1, J 6.8 Hz, CH); δ 7.32–8.17 (m, 9, CH$_{arom}$ and 2×NH$_2$)(; δ 8.50 (s, 1, H3).

$^{13}$C NMR (d$^6$DMSO) δ 11.1 (q, CH$_3$); δ 11.6 (q, CH$_3$); δ 25.5 (t, CH$_2$); δ 25.9 (t, CH$_2$); δ 48.5 (d, CH); δ 50.4 (d, CH); δ 110.2 (s, C3a); δ 120.8 (d, C2', C6'); δ 126.8 (d, C4'); δ 129.3 (d, C3', C5'); δ 133.8 (d, C-3); δ 138.2 (s, C1'); δ 151.1 (s, C7a); δ 164.5 (s, C4); δ 168.2 (s, C6); δ 171.5 (s, C=O), δ 172.0 (s, C=O).

IR 3360, 3200, 1660, 1650 cm$^{-1}$.

COMPOUND 5

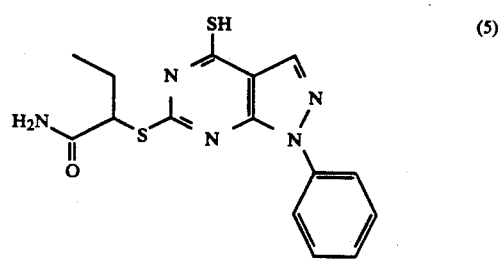
(5)

Hydrophobic Binding Domain—Phenyl ring.
Central Aromatic Binding Domain—Pyrimidine ring.
Ribose Binding Domain—Amide side chain (C6).

The IC$_{50}$ at the A$_1$ receptor ($^3$H-PIA) is 4.92($\pm$1.06)$\times$10$^{-7}$M.

6-α-carbamoylpropylthio-4-mercapto-1-phenyl-pyrazolo[3,4-d]pyrimidine

The above method with one equivalent of 2-bromobutanamide afforded pure 6-α-carbamoylpropylthio-4-mercapto-1-phenylpyrazolo[3,4-d]pyrimidine: yield 67%: mp 227°–237° C.

$^1$H NMR (d$^6$DMSO) δ 0.99 (t, 3, J 7.2 Hz, CH$_3$); δ 1.98 (m, 2, J 6.7, 7.2 Hz, CH$_2$); δ 4.35 (t, 1, J 6.7 Hz, CH); δ 7.40–8.55 (m, 8, CH$_{arom}$, NH and SH); δ 8.36 (s, 1, H3).

$^{13}$C NMR (d$^6$DMSO) δ 11.4 (q, CH$_3$); δ 25.6 (t, CH$_2$); δ 50.8 (d, CH); δ 116.4 (s, C3a); δ 121.3 (d, C2', C6'); δ 127.1 (d, C4'); δ 129.3 (d, C3', C5'); δ 138.0 (s, C1'); δ 138.1 (d, C3); δ 146.4 (s, C7a); δ 160.3 (s, C6); δ 171.0 (s, C=O); δ 180.1 (s, C4).

IR 3375, 2960, 2850, 1660 cm$^{-1}$.

COMPOUND 6

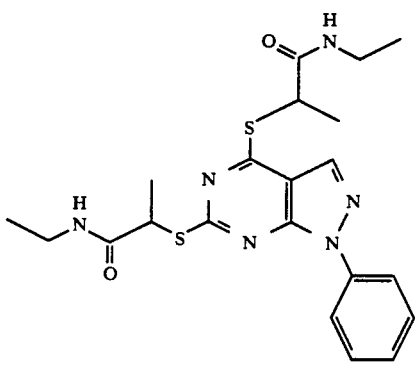

(6)

Hydrophobic Binding Site—Phenyl ring.
Central Aromatic Binding Domain—Pyrimidine ring.
Ribose Binding Domain—Amide side chain (C6).

The IC$_{50}$ at the A$_1$ receptor ($^3$H-PIA) is 5.8($\pm$2.1)$\times$10$^{-7}$M.
The IC$_{50}$ at the A$_2$ receptor ($^3$H-CGS21680) is 5.7($\pm$0.4)$\times$10$^{-7}$M.

4,6-Bis-α-N-ethylcarbamoylethylthio-1-phenyl-pyrazolo[3,4-d]pyrimidine.

1-Phenyl-5H,7H-pyrazolo[3,4-d]pyrimidin-4,6-dithione (0.67 g; 2.6 mmol) was stirred in sodium hydroxide (1M, 5 ml). To the solution, N-ethyl-2-bromopropionamide (1.19 g, 7.0 mmol) was added. Within 5 min, a white precipitate formed. After 30 min, the solid was filtered, washed with cold deionized water (2×5 ml) and dried (1.00 g, 85% crude yield). The compound was recrystalized from DMSO and water to yield 0.75 g of. The product is a mixture of diasteriomers. NMR data shows duplicates of each peak as expected 4,6-Bis-α-N-ethylcarbamoylethylthio-1-phenylpyrazolo]3,4-b[pyrimidine.

$^1$H NMR (d$^6$DMSO): δ 0.96 (3H, t, CH$_3$, J 7.1 Hz); δ 1.05 (3H, t, CH$_3$, J 7.1 Hz); δ 1.58 (3H, d, CH$_3$, J 6.9 Hz); δ 3.08 (4H, m, CH$_2$); δ 4.51 (1H, m, CH); δ 4.77 (1H, m, CH); δ 7.42–8.18 (5H, m, CH$_{arom}$); δ 8.24 (1H, t (broad), NH$_{amide}$, J 4.3 Hz); δ 8.38 (1H, t (broad), NH$_{amide}$, J 4.9 Hz); δ 8.52 (1H, s, N=CH);

$^{13}$C NMR (d$^6$DMSO): δ 14.24 (CH$_3$); δ 18.15 (CH$_3$); δ 18.85 (CH$_3$); δ 33.70 (CH$_2$); δ 42.72 (CH); δ 44.07 (CH); δ 110.14 (C3a); δ 120.86 (C2', C6'); δ 126.76 (C4'); δ 129.36 (C3', C5'); δ 133.80 (C3); δ 138.16 (C1'); δ 151.04 (C7a); δ 164.34 (C4); δ 168.01 (C6); δ 169.88 (C=O); δ 170.40 (C=).

COMPOUND 7

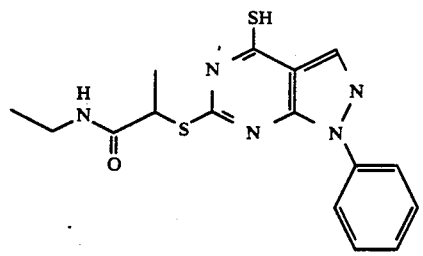

(7)

Hydrophobic Binding Site—Phenyl ring.
Central Aromatic Binding Domain—Pyrimidine ring.
Ribose Binding Domain—Amide side chain (C6).

The IC$_{50}$ at the A$_1$ receptor ($^3$H-PIA) is 4.9($\pm$0.9)$\times$10$^{-7}$M.
The IC$_{50}$ at the A$_2$ receptor ($^3$H-CGS21680) is 5.4(−1.1($\times$10$^{-7}$M.

6-α-N-Ethylcarbamoylethylthio-4-mercapto-1-phenyl-pyrazolo[3,4-d]pyrimidine

1-Phenyl-5H,7H-pyrazolo[3,4-d]pyrimidin-4,6-dithione (0.43 g, 2.4 mmol) was stirred in dry pyridine under nitrogen at room temperature. To the suspensions, N-ethyl-2-bromopropionamide (0.49 g, 1.9 mmol). Within 5 min, a precipitate formed, and a further 6 ml of dry pyridine was added. The mixture was stirred for 30 min. Ethyl acetate (10 ml) was added and the precipitate filtered via vacuum filtration, washed with ethyl acetate (2×10 ml). The precipitate weighed 0.50 g (50% crude yield). Cooling of the mother liquors afforded the second fraction. The precipitate was filtered, dried and this was pooled with the first crop to yield 0.68 g (89% crude yield). The compound was recrystalised from DMSO and water to yield 6-α-N-Ethylcarbamoylethylthio-4-mercapto-1-phenylpyrazolo[3,4-d]pyrimidine.

$^1$H NMR (d$^6$DMSO): δ 0.93 (3H, t, CH$_3$, J 7.1); δ 1.59 (3H, d, CH$_3$, J 7.1); δ 3.01 (2H, m, CH$_2$, J 7.0); δ 4.42 (1H, q, CH, J 7.0); δ 7.42–8.15 (5H, CH$_{arom}$); δ 8.32 (1H, t, NH$_{amide}$); δ 8.45 (1H, s, N=CH); δ 10.45 (1H, s (broad), SH);

$^{13}$C NMR (d$^6$DMSO): δ 14.14 (CH3); δ 1820 (CH3); δ 33.70 (CH$_2$); δ 44.67 (CH); δ 116.37 (C3a); δ 121.27 (C2', C6'); δ 127.06 (C4'); δ 129.35 (C3', C5'); δ 137.98 (C1'); δ 138.12 (C3); δ 146.43 (C7a); δ 160.09 (C6); δ 169.57 (C4); δ 180.13 (C=O).

COMPOUND 8

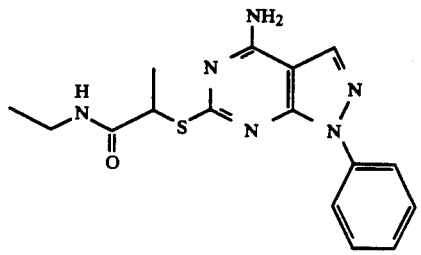

(8)

Hydrophobic Binding Site—Phenyl ring.

Central Aromatic Binding Domain—Pyrimidine ring.

Ribose Binding Domain—Amide side chain (C6).

The $IC_{50}$ at the $A_1$ receptor ($^3$H-PIA) is $1.7(\pm 0.5) \times 10^{-8}$M.

6-Amino-4-α-N-ethylcarbamoylethylthio-1-phenyl-pyrazolo[3,4-d]pyrimidine

6-α-N-Ethylcarbamoylethylthio-4-mercapto-1-phenylpyrazolo[3,4-d]pyrimidine (1.65 g, 4.59 mmol) was dissolved in sodium hydroxide (10 ml, 1M). Methyl iodide (0.34 ml, 5.5 mmol) was added. The solution was stirred at room temperature for 30 min. A white precipitate formed which was filtered via suction filtration, and dryed (1.56 g, 91% crude yield). The compound was recrystalised from DMSO and water to give 6-α-N-Ethylcarbamoylethylthio-4-methylthio-1-phenyl-pyrazolo[3,4-d]pyrimidine.

$^1$H NMR (d$^6$DMSO): δ 0.91 (3H, t, CH$_3$, J 7.1); δ 1.62 (3H, d, CH$_3$, J 7.1); δ 2.68 (3h, s, CH$_3$); δ 3.08 (2H, m, CH$_2$); δ 4.52 (1H, q, CH J 7.1); δ 7.35–8.15 (5H, CH$_{arom}$); δ 8.23 (1H, t, NH$_{amide}$); δ 8.51 (1H, s, N=CH).

Ammonia was bubbled into a suspension of 6-α-N-ethylcarbamoylethylthio-4-methylthio-1-phenyl-pyrazolo[3,4-d]pyrimidine (0.20 g, 0.54 mmol) in dry DME/ethanol (15 ml, 1:1 mixture). The mixture was sealed under an atmosphere of dry nitrogen and heated to 115° C. for 48 hrs. After this time, a fine beige precipitate had formed. This was filtered via vacuum suction and dryed (0.1294 g, 71% crude yield). The product was recrystalized from DMSO and water to yield pure 6-Amino-4-α-N-ethylcarbamoylethylthio-1-phenyl-pyrazolo[3,4-d]pyrimidine.

$^1$H NMR (d$^6$DMSO): δ 0.88 (3H, t, CH$_3$, J 7.1); δ 1.55 (3H, d, CH$_3$, J 7.1); δ 3.06 (2H, m, CH$_2$); δ 4.41 (1H, q, CH, J 7.1); δ 7.28–8.23 (2H; 5H, CH$_{arom}$; 2H, NH$_2$ and 1H, NH$_{amide}$); δ 8.31 (1H, s, N=CH).

Compound 4 by the process of the invention had its structure determined by the model set out in FIGS. 6 and 7. It had already been shown in FIG. 3 that the amide functionalities of NECA and substituted pyrazolo [3,4-d] pyrimidines were in close proximity. Compound 4 fits the model with the phenyl ring occupying the hydrophobic domain, the pyrimidine ring occupying the aromatic domain and the amide side chain occupying the ribose domain. The amide side chain occupies the area of space of the ribose domain in both the A1 and A2 orientations. The butanamide side chain increased potency over the proprionamide moiety in FIG. 3.

Compound 5 was determined by removing a superfluous group which was the C4 butanamide group.

Compound 6 was determined by analogy with the orientation of CGS 21680 shown in FIG. 4. The N-ethyl side chain was added in place of one of the hydrogens.

Compound 7 had its structure determined by the process leading to the determination of the structure of compound 5 removing the superfluous C$_4$-N-ethyl butanamide group and replacing this group with hydrogen.

Compound 8 had its structure determined by introduction of an —NH$_2$ group corresponding to the position of the —NH$_2$ group as in FIGS. 6 and 7 and also shown in FIG. 4.

From the foregoing, it therefore will be appreciated that the determination of appropriate antagonists and agonists would be very beneficial. As described previously, adenosine has been shown to be a neuromodulator and to have a homeostatic role in the CNS. The central stimulant action of the xanthenes, caffeine and theophylline, has been shown to occur because of antagonism of the effects of extracellular adenosine. Selective CNS agonists would be sedatives or somnificants, selective CNS antagonists would be central stimulants. Adenosine has been implicated in anxiety, analgesia and aging. As stated previously, it has been shown that adenosine may be the brain's natural anticonvulsant, that adenosine is involved in the spontaneous arrest of epileptic seizures and that it is brought into play by the seizure itself. Adenosine agonists have anticonvulsant activity. Adenosine has also been shown to be a putative mediator in asthma and adenosine-induced bronchoconstriction is selective for allergic and asthmatic subjects. Locally produced adenosine is an important physiological regulator of coronary vascular resistance in mammalian hearts acting via adenosine receptors. Selective A2 - adenosine agonists would relax coronary vascular smooth muscle and avoid the negative inotropic and chronotropic responses associated with A1-adenosine receptors thus providing useful hypotensive agents.

The invention therefore involves syntheses of several series of compounds based on the foregoing.

Selective A1 and A2 agonists or antagonists have a large potential in therapeutics with possible applications in the central and peripheral nervous system, and in the cardiovascular area.

Thus, the invention contemplates the following:

(a) synthesis of potential agonists and antagonists for the adenosine receptors;

(b) investigation of the activity of the synthesised compounds by a variety of radioligand binding and biochemical techniques; and Thus, in accordance with the invention it is proposed that:

(a) the development of specific agonists and antagonists is necessary to fully elucidate the role of adenosine receptors in CNS and cardiovascular function;

(b) potential therapeutic use of agonists in the CNS as sedatives or somnificants, as anti-epileptics and in the cardiovascular system as hypotensives could ensure. Potential therapeutic use of antagonists as central stimulants and as bronchodilators could ensue.

We claim:

1. The compound (5)

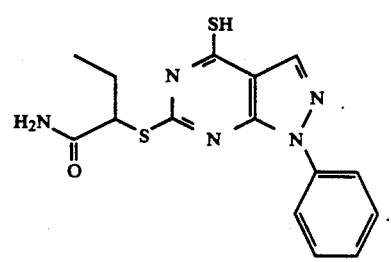

2. The compound (7)

15
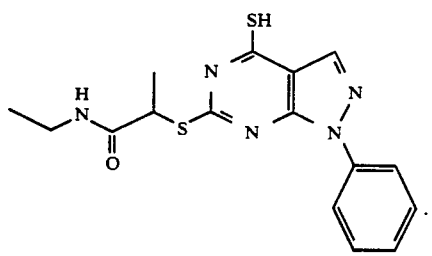
3. The compound (8)
16
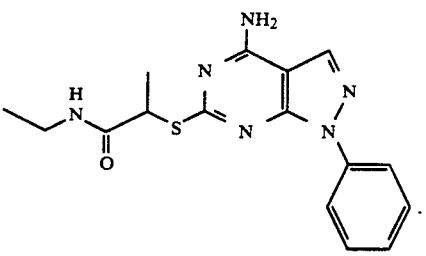
* * * * *